(12) United States Patent
Lin

(10) Patent No.: US 12,415,976 B2
(45) Date of Patent: Sep. 16, 2025

(54) SYSTEM AND METHOD FOR BIOLOGICAL METHANE GAS GENERATION AND REMOVAL OF CARBON DIOXIDE THEREFROM

(71) Applicant: UCHICAGO ARGONNE, LLC, Chicago, IL (US)

(72) Inventor: YuPo J. Lin, Naperville, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 1096 days.

(21) Appl. No.: 17/137,956

(22) Filed: Dec. 30, 2020

(65) Prior Publication Data

US 2022/0204899 A1 Jun. 30, 2022

(51) Int. Cl.
*C12M 1/107* (2006.01)
*B01D 53/18* (2006.01)
(Continued)

(52) U.S. Cl.
CPC ........... *C12M 21/04* (2013.01); *B01D 53/185* (2013.01); *B01D 53/326* (2013.01);
(Continued)

(58) Field of Classification Search
CPC .. B01D 61/445; B01D 61/466; B01D 61/468; B01D 61/48; Y02C 20/40; C25B 9/70–77; C02F 1/469
See application file for complete search history.

(56) References Cited

U.S. PATENT DOCUMENTS 4,549,946 A * 10/1985 Horn .................... B01D 61/445
204/DIG. 13
4,871,431 A * 10/1989 Parsi .................... C02F 1/4695
204/632

(Continued)

OTHER PUBLICATIONS

Enzmann, F. et al., Methanogens: Biochemical Background and Biotechnological Applications, AMB Express 8(1), 1-22 (2018).
(Continued)

*Primary Examiner* — Luan V Van
*Assistant Examiner* — Andrew Koltonow
(74) *Attorney, Agent, or Firm* — Olson & Cepuritis, Ltd.

(57) ABSTRACT

A system for biological methane production and removing carbon dioxide from the methane comprises (a) a primary anaerobic digester adapted and arranged to generate a gaseous mixture comprising methane and carbon dioxide from organic materials; (b) an electrochemical reactor comprising at least one reactor cell including an anode spaced from a cathode by a porous ion exchange resin wafer with a cation exchange membrane between the anode and the resin wafer and a bipolar ion exchange membrane between the cathode and the resin wafer; the electrochemical reactor being adapted and arranged to capture gaseous carbon dioxide within the resin wafer as aqueous bicarbonate, and to electrochemically generate hydrogen gas at the cathode; and (c) a hydrogenotrophic methanogenesis bioreactor adapted and arranged to convert the bicarbonate and hydrogen from the electrochemical reactor to methane. An electrochemical reactor and a method for producing methane with reduced carbon dioxide content also are described.

19 Claims, 7 Drawing Sheets

(51) Int. Cl.
*B01D 53/22* (2006.01)
*B01D 53/32* (2006.01)
*B01D 61/44* (2006.01)
*B01D 61/46* (2006.01)
*B01D 61/48* (2006.01)

(52) U.S. Cl.
CPC ......... *B01D 61/445* (2013.01); *B01D 61/466* (2022.08); *B01D 61/485* (2013.01); *B01D 2053/221* (2013.01); *B01D 2257/504* (2013.01); *B01D 2273/10* (2013.01); *B01D 2275/30* (2013.01)

(56) References Cited

U.S. PATENT DOCUMENTS

| | | | |
|---|---|---|---|
| 5,954,935 A * | 9/1999 | Neumeister | B01D 61/48 204/632 |
| 6,495,014 B1 | 12/2002 | Datta et al. | |
| 7,306,934 B2 | 12/2007 | Arora et al. | |
| 7,452,920 B2 | 11/2008 | Lin et al. | |
| 8,535,502 B2 * | 9/2013 | Littau | B01D 53/96 204/534 |
| 8,679,314 B1 | 3/2014 | Snyder et al. | |
| 8,864,963 B2 | 10/2014 | Lin et al. | |
| 9,126,150 B2 | 9/2015 | Lin et al. | |
| 9,339,764 B2 | 5/2016 | Lin et al. | |
| 2013/0180863 A1 * | 7/2013 | Kaczur | C25B 15/08 205/349 |
| 2013/0233715 A1 * | 9/2013 | Lin | B01D 61/48 204/632 |
| 2022/0144673 A1 * | 5/2022 | Xiang | C02F 1/46109 |

OTHER PUBLICATIONS

Ho, D. et al., High-Rate, High Temperature Acetotrophic Methanogenesis Governed by A Three Population Consortium in Anaerobicc Bioreactors, PLOS One 11(8), 1-13 (2016).

Lackner, N. et al., Research Article: Hydrogenotrophic Methanogenesis and Autotrophic Growth of Methanosarcina Thermophila, Hindawi Archaea Article ID 4712608, 1-8 (2018).

Liu, H. et al., Selective Acetate Production With CO2 Sequestration Through Acetogen-Enriched Sludge Inoculums In Anaerobic Digestion, Biochemical Engineering Journal 121, 163-170 (2017).

Westerholm, M. et al., Biogas Production Through Syntrophic Acetate Oxidation and Deliberate Operating Strategies Fo Improved Digester Performance, Applied Energy 179, 124-135 (2016).

Renewable Biological Systems For Alternative Sustainable Energy Production (FAO Agricultural Services Bulletin-128), Chapter 4, Methane Production, 1-15, Edited by Kazuhisa Miyamoto (1997).

* cited by examiner

SYSTEM AND METHOD FOR BIOLOGICAL METHANE GAS GENERATION AND REMOVAL OF CARBON DIOXIDE THEREFROM

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to a system and method for generating methane from biological waste materials and removing carbon dioxide from the methane using an electrochemical apparatus.

BACKGROUND OF THE INVENTION

Efficient capture and removal of carbon dioxide from biologically generated methane gas is an essential technology for the development of more environmentally acceptable waste-based energy production systems. Converting carbon dioxide produced in wastewater treatment to energy is a strategy for ensuring water and energy resilience. Using renewable resources such as solar and wind for carbon dioxide utilization is also an important strategy to reduce the impact of greenhouse gasses on climate change. Biological conversion of organic materials such as food waste, wastewater and waste treatment sludge can use used on a large scale. For example, carbon dioxide produced in anaerobic digesters and flue gasses can be converted to methane in hydrogenotrophic methanogenesis bioreactors.

Although microbial populations in bioreactors are robust with respect to toxic compounds in the feed streams there are still challenges in anaerobic gas fermentation to produce methane, including (1) the low aqueous solubility of carbon dioxide and (2) obtaining a suitable, convenient and cost effective source of hydrogen. The low solubility of carbon dioxide leads to low carbon dioxide utilization in bioreactors operated in open systems as atmospheric pressure. The source, production cost and storage of hydrogen frequently makes the economics and investment potential of biological methane production unfavorable.

Because of the aforementioned challenges there is an ongoing need for alternative processes for biological production of methane from organic/biological waste streams.

SUMMARY OF THE INVENTION

A system and method for biological methane gas production and removing carbon dioxide from the methane is described herein. The system comprises (a) a primary anaerobic digester adapted and arranged to generate a gaseous mixture comprising methane and carbon dioxide from organic materials; (b) an electrochemical reactor comprising at least one reactor cell including an anode spaced from a cathode by a porous ion exchange resin wafer with a cation exchange membrane between the anode and the resin wafer and a bipolar ion exchange membrane between the cathode and the resin wafer; the electrochemical reactor being adapted and arranged to capture gaseous carbon dioxide within the resin wafer as aqueous bicarbonate, and to electrochemically generate hydrogen gas at the cathode; and (c) a hydrogenotrophic methanogenesis bioreactor adapted and arranged to convert the bicarbonate and hydrogen from the electrochemical reactor to methane. The primary anaerobic digester includes a gas transfer line in fluid communication with an inlet end of the electrochemical reactor adapted and arranged to receive gas and liquid into pores of the resin wafer. The electrochemical reactor further includes a first gas vent line; an outlet operably connected to a liquid transfer line in fluid communication with the hydrogenotrophic methanogenesis bioreactor; and a hydrogen transfer line providing fluid communication between the hydrogenotrophic methanogenesis bioreactor and a region adjacent to the cathode where hydrogen is produced during use. The hydrogenotrophic methanogenesis bioreactor comprises: a liquid recycle line in fluid communication with the inlet end of the electrochemical reactor adapted and arranged to direct fluid flow through the electrochemical reactor; and a second gas vent line.

In use, a gaseous mixture containing methane and carbon dioxide is formed from the organic materials in the primary anaerobic digester. The electrochemical reactor is filled with an aqueous fluid, and the gaseous mixture from the primary anaerobic digester is transferred into the inlet end of the electrochemical reactor via the gas transfer line to flow through the resin wafer while a voltage is applied across the cathode and the anode of the electrochemical reactor. The carbon dioxide from the gaseous mixture is electrochemically converted to bicarbonate in the aqueous fluid within electrochemical reactor; while hydrogen simultaneously is electrochemically generated at the cathode. The methane from the gaseous mixture and the aqueous fluid both flow through the resin wafer, and carbon dioxide-depleted methane is vented through the first gas vent line and stored for later use. The aqueous fluid containing the bicarbonate flows through the liquid transfer line into the hydrogenotrophic methanogenesis bioreactor, and the hydrogen generated at the cathode flows through the hydrogen transfer line into the hydrogenotrophic methanogenesis bioreactor. The bicarbonate and hydrogen are biologically converted to methane in the hydrogenotrophic methanogenesis bioreactor, and the methane is vented through the second gas vent line and collected for later use. Aqueous fluid is recycled back into the inlet end of the electrochemical reactor from the hydrogenotrophic methanogenesis bioreactor through the liquid recycle line to maintain a flow of liquid within the electrochemical reactor when in use.

The tandem electrochemical and gas-phase bioreactor system and method described herein provide a number of advantages for biological methane production. For example, the system generates high-purity renewable methane rather than just biogas (a mixture of methane and carbon dioxide). In addition, utilizing electrochemically produced hydrogen and carbon dioxide captured as aqueous bicarbonate in a hydrogenotrophic methanogenesis bioreactor boosts the overall methane production by at least about 40% and reduces capital and production costs by at least about 20% compared to traditional anaerobic digestion processes.

The primary anaerobic digester of system can comprise a dual reactor that includes (i) an acidogenesis reactor adapted and arranged to biologically convert organic waste and wastewater to soluble volatile fatty acids (VFA), methane, carbon dioxide, and hydrogen; and (ii) an acetoclastic methanogenesis reactor adapted and arranged to biologically convert the VFA to carbon dioxide and methane. The gas transfer line of the dual reactor is in fluid communication with both the acidogenesis reactor and the acetoclastic methanogenesis reactor; and the acidogenesis reactor is in fluid communication with the acetoclastic methanogenesis reactor via a liquid feed line.

In use, VFA, carbon dioxide, hydrogen and methane are generated in the acidogenesis reactor, and VFA-containing liquid from the acidogenesis reactor is fed into the acetoclastic methanogenesis reactor via the liquid feed line. Methane and carbon dioxide are generated in the acetoclastic methanogenesis reactor from the VFA, and carbon dioxide, methane, and hydrogen are transferred from the acidogenesis reactor and the acetoclastic methanogenesis reactor into the inlet end of electrochemical reactor through the gas transfer line.

A preferred electrochemical reactor, also referred to as "electrochemical reactor for carbon and hydrogen delivery" (ERCHD), comprises a plurality (e.g., 2 to about 100) of the electrochemical reactor cells in a stack with the cathode of each adjacent cell separated from the anode of the nearest adjacent cell by an electrical insulator; and the reactor cells are in fluid communication with each other in series so that liquid and gas flow through each resin wafer sequentially. Each wafer can have a thickness in the range of about 1 to about 20 mm.

Optionally, the electrochemical reactor includes at least one a porous gas and liquid flow distributor in contact with the resin wafer(s). The flow distributor is adapted and arranged to laterally distribute gas and liquid within pores thereof prior to entering the resin wafer of the electrochemical reactor. Preferably, the flow distributer includes interconnected pores having an average pore size in the range of about 100 to about 600 micrometers, and is adapted and arranged to laterally distribute the liquid and gas bubbles having an average diameter in the range of about 100 to about 600 micrometers throughout the flow distributor and into the resin wafer of the electrochemical reactor. Optionally, flue gas can be introduced into the electrochemical reactor along with the gases from the anaerobic digester to supplement the carbon dioxide from the digester.

A method for biologically generating carbon dioxide-depleted biogas comprises the steps of:

(a) generating a biogas comprising methane and carbon dioxide by anaerobic degradation of biological material in an anaerobic digester;
(b) passing the biogas generated in step (a) through an electrochemical reactor comprising an anode spaced from a cathode by a porous ion exchange resin wafer with a cation exchange membrane between the anode and the resin wafer and a bipolar ion exchange membrane between the cathode and the resin wafer, while applying a voltage across the anode and the cathode to convert carbon dioxide in the biogas to bicarbonate and to generate hydrogen gas by electrochemical hydrogen evolution at the cathode from protons produced by an electrochemical water splitting reaction occurring on the bipolar membrane surface;
(c) venting and collecting the methane from the biogas that passes through the electrochemical reactor;
(d) passing the hydrogen and bicarbonate formed in step (b) into a hydrogenotrophic methanogenesis bioreactor;
(e) generating methane from the hydrogen and bicarbonate in the hydrogenotrophic methanogenesis bioreactor; and
(f) venting and collecting the methane that forms in the hydrogenotrophic methanogenesis bioreactor.

In some embodiments of the method, the anaerobic digester comprises: (i) an acidogenesis reactor adapted and arranged to biologically convert organic waste and wastewater to soluble volatile fatty acids (VFA), methane, carbon dioxide, and hydrogen; and (ii) an acetoclastic methanogenesis reactor adapted and arranged to biologically convert the VFA to carbon dioxide and methane. In use, VFA, carbon dioxide, hydrogen and methane are generated in the acidogenesis reactor; VFA-containing liquid from the acidogenesis reactor is fed into the acetoclastic methanogenesis reactor; methane and carbon dioxide are generated in the acetoclastic methanogenesis reactor, and carbon dioxide, methane, and hydrogen are transferred from the acidogenesis reactor and the acetoclastic methanogenesis reactor into electrochemical reactor.

The systems, electrochemical reactors, and methods described herein comprise certain novel features and a combination of parts hereinafter fully described, which are illustrated in the accompanying drawings, and particularly pointed out in the appended claims. It is to be understood that various changes in the details may be made without departing from the spirit, or sacrificing any of the advantages of the systems, electrochemical reactors, and methods described herein.

DETAILED DESCRIPTION OF THE PRESENT INVENTION

Figure 1A:
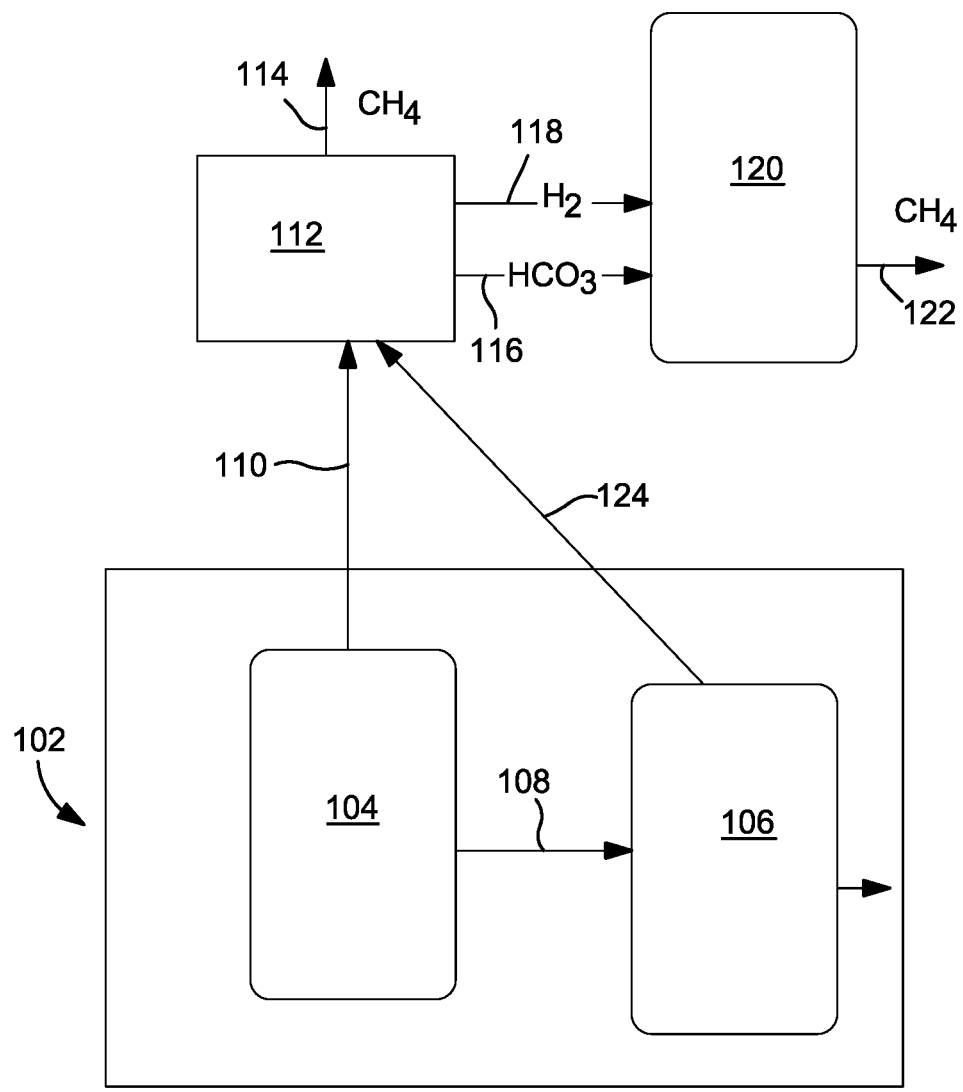
FIG. 1A provides a schematic illustration of a system for biologically generating a methane-containing biogas and removing carbon dioxide from the biogas as bicarbonate, comprising a primary anaerobic digester connected to an electrochemical reactor for removing carbon dioxide from the biogas and electrochemically generating hydrogen, and a hydrogenotrophic methanogenesis bioreactor for converting the hydrogen and bicarbonate into additional methane.

The organic fraction of municipal solid waste comprises more than 50% of the almost 300 million tons of municipal solid waste generated in the U.S. per year. This fraction is difficult to recycle, and the majority of this waste is landfilled. An additional 55 million dry tons of water resource recovery facility residuals and manure slurries are produced per year. These potential energy sources are largely untapped as waste-to-energy technologies are currently expensive to build and demanding to operate and maintain. The increase in efficiency and reduction in cost resulting from the successful development of the systems and methods described herein can substantially reduce the gasoline gallon equivalent of renewable methane and propel waste-produced renewable energy to become financially favorable.

The systems and methods described herein couple biological methanogenesis and electrochemical conversion of carbon dioxide and hydrogen generation to efficiently form high purity renewable methane at a significantly methane higher production rate than conventional, state of the art biological methanation processes. The systems and methods utilize three processing stages including anaerobic digestion of organic materials (e.g., wastewater, sludge, food waste, etc.) to produce a biogas, an electrochemical reactor to capture and remove carbon dioxide from the biogas for form aqueous bicarbonate, while simultaneously electrochemically generating hydrogen, and finally hydrogenotrophic methanogenesis to convert the bicarbonate and hydrogen into more methane. Overall, by combining carbon dioxide capture with hydrogen production, the systems and methods described herein is estimated to boost the overall methane production rate from anaerobic digestion of organic matter by up to 40% while reducing production costs by at least about 20%.

Anaerobic digestion involves hydrolysis, acidogenesis, acetogenesis, and methanogenesis of organic materials (e.g., food waste, wastewater, waste-treatment sludge, and the like). Hydrolysis involves solubilization of particulates and depolymerization of complex materials such as proteins and carbohydrates. Acidogenesis is a process in which the hydrolyzed materials are converted to volatile fatty acids (low molecular weight organic acids). Acetogenesis is a process in which the volatile fatty acids are converted to acetic acid, carbon dioxide and hydrogen. Methanogenesis is a process the utilizes the acetic acid and hydrogen from the acetogenesis process to produce methane and carbon dioxide. These four stages typically occur together in an anaerobic digester.

Anaerobic digestion systems can be separated into an acetogenesis stage and a methanogenesis stage. In acetogenesis, acidogenic microorganisms (acidogens) and hydrogen-producing microorganisms generate hydrogen and volatile fatty acids (VFAs). In methanogenesis, acetogenic microorganisms (acetogens) and methane producing microorganisms (methanogens) convert the VFAs into methane (see, e.g., S. Li, X. Yang, in Handbook of Biofuels Production (Second Edition), 2016).

Hydrolysis involves bacteria such as bacterial form the genera *Bacillus, Cellulomonas* and *Eubacterium*. Acidogensis involves bacterial from genera such as *Propionibacterium, Butyrivibrio* and *Acetivibrio*. Acetogenesis involves bacteria from genera such as Clostridia and *Acetivibrio*, in particular *Clostridium aceticum, Acetobacter woodii* and *Clostridium termautotrophicum*. Methanogsesis involves microorganisms of the order Archaea, which are phylogenetically distinct from both eukaryotes and bacteria, but are often found in association with anaerobic bacteria. Methanogens belong to the phylum Euryarchaeota in five orders that include Methanobacteriales, Methanococcales, Methanomicrobiales, Methanopyrales, and Methanosarcinales. Methanogens do not utilize oxygen for respiration. Instead, methanogens use carbon as the terminal electron acceptor in methanogenesis. The carbon generally comes from low molecular weight organic compounds. The two well described pathways for methanogenesis involve the use of acetic acid or inorganic carbon dioxide as terminal electron acceptors (see Equations (Eq.) 1 and 2):

$$CO_2 + 4H_2 \rightarrow CH_4 + 2H_2O \qquad \text{Eq. 1:}$$

$$CH_3COOH \rightarrow CH_4 + CO_2 \qquad \text{Eq. 2:}$$

Acetogenesis can be illustrated by Equation 3:

$$2CO_2 + 4H_2 \rightarrow CH_3COOH + 2H_2O \qquad \text{Eq. 3.}$$

There are three pathways for methanogenesis. Acetoclastic methanogenesis converts acetate to methane and carbon dioxide by Equation 2 described above.

Acetoclastic methanogens include the Methanosarcinales, such as *Methanosarcina* and *Methanosaeta*. Methylotrophic methanogenesis utilizes methanol and methylamine as the source of carbon for methane production. Hydrogenotrophic methanogenesis, which occurs in all five of the Euryarchaeota methanogenic orders described above, use hydrogen for the reduction of carbon dioxide according to Equation 1 described above, or reduction of CO or formate by similar processes.

Anaerobic digesters such as acteogenic reactors and methanogenic reactors are described, e.g., in United Nations Food and Agriculture Organization (FAO) Agricultural Services Bulletin-128, "Renewable biological systems for alternative sustainable energy production", Chapter 4, 1997, available online at the fao.org website; which is incorporated herein by reference in its entirety.

In the electrochemical reactors described herein, carbon dioxide is captured as bicarbonate by reaction with electrochemically produced hydroxide in the resin wafers. Preferably, in use, the pH of fluid within the resin wafer of the electrochemical reactor is maintained in the range of about 7.5 to about 9.5 by the electric potential applied across the anode and the cathode. Typically, the electric potential applied across the anode and cathode is at least above 1.23 Volt (e.g., about 1.23 to about 5 Volts) per reactor cell for a desired current. The actual voltage per reactor cell pair will vary with the thickness of the resin wafer, as will be evident to those of ordinary skill in the art. Thicker wafers will require higher voltages. Preferably, the voltage per cell pair will be greater than 1.23 V if the wafer thickness is greater than 1 mm. Typically, the wafers will have a thickness in the range of about 1 mm to about 20 mm. However, greater wafer thickness may still work. The determination of an appropriate working voltage is within the level of ordinary skill in the art.

In some preferred embodiments, a porous gas distributor is positioned across the inlet end of each wafer. The distributor comprises a porous polymeric foam or sintered material with interconnected pores positioned in close contact with or integral with the inlet end of each wafer, such that liquid and gas entering the distributor are dispersed laterally through the porous material of the distributor before entering the resin wafer. The lateral dispersion of the gas in the porous distributor provides an even plug-flow distribution of the gas and fluid, which reduces gas channeling in the wafers during operation of the electrochemical reactor.

The porous gas and liquid distributors ("porous distributors") can be included as separate pieces that are arranged in close contact across the inlet end of the wafer. Alternatively, the porous distributors can be integral with (e.g., fused to) the wafers. In preferred embodiments, the porous distributors are formed from a porous polymeric foam (e.g., polyurethane or polyethylene foam). Each porous distributor is adapted for introducing $CO_2$-containing gas bubbles into an aqueous fluid within the resin wafer to direct an even distribution of micro-sized gas bubbles into the resin wafer to facilitate conversion of $CO_2$ from the biogas into bicarbonate ion. The aqueous fluid and gas are laterally dispersed and mixed together as they pass through the interconnected pores of the distributor and into the wafer. The porous distributor disperses the gas into micro-sized bubbles, and creates an even "plug-flow" distribution in the aqueous fluid carrier entering the wafer.

As used herein, the terms "micro-sized gas bubbles", "microbubbles", and grammatical variations thereof, refer to gas bubbles having a diameter of less than about 1000 micrometers. The size (i.e., volume) of the pores of the gas distributor influences the size of gas bubbles produced therein. Preferably, the porous distributor has an average pore diameter of about 100 to about 600 micrometers. While it is understood that the pores of the gas distributor may not be spherical in shape, for convenience, the phrase "average pore size of about 100 micrometers" refers to pores having a volume equivalent to the volume of a sphere having a diameter of 100 micrometers. Such gas and liquid flow distributors are described, e.g., in co-owned U.S. Pat. No. 9,339,764 to YuPo J. Lin et al., which is incorporated herein by reference in its entirety.

The electrochemical reactor also is adapted to vent $CO_2$-depleted methane-containing gas from the reactor. Gas as can be introduced into or vented from the wafers or portions thereof via gas inlet and/or outlet tubes, via microporous membranes or channels in contact with or connected to the wafers or portions, or by any other suitable structure. The cathodes, resin wafers with their accompanying gas distributors, and anodes are interleaved with alternating cation exchange and bipolar membranes and collectively direct a net flow of protons through the wafers toward the direction of the cathode and a net flow of hydroxyl ions through the wafers toward the direction of the anode when an electric potential is applied to across cathode and anode. The flow of protons and hydroxyl ions, combined with the capture of $CO_2$, maintains a basic pH in each basic wafer or basic portion and an acidic pH in each acidic wafer or acidic portion. Hydrogen gas is electrochemically generated at the cathode aided by water splitting facilitated by the bipolar membrane. Anodes and cathodes of adjacent reactor cells are separated by an electrical insulator such as a non-conducting polymer.

Porous solid resin wafer ion exchange materials suitable for use in the present invention can be prepared in any suitable manner known in the art, such as for example the materials and methods described in U.S. Pat. No. 6,495,014 (Datta et al., incorporated herein by reference in its entirety), U.S. Pat. No. 7,452,920 (Lin et al., incorporated herein by reference in its entirety), and U.S. Pat. No. 7,306,934 (Arora et al.). Commercial resin wafers are also available than can be used or adapted for use in the electrochemical reactors described herein.

FIG. 1A provides a schematic illustration of a system for biologically generating a methane-containing biogas and removing carbon dioxide from the biogas as bicarbonate, generating hydrogen, and converting the bicarbonate and hydrogen into methane. System 100 comprises a two-stage primary anaerobic digester system 102 including acidogenesis reactor 104 and acetoclastic methanogenesis reactor 106. A liquid feed line 108 provides for transfer of VFA-containing liquid from reactor 104 to reactor 106. Acidogenesis reactor 104 includes a gas transfer line 110 for transferring gases generated in reactor 104 into ERCHD electrochemical reactor 112. Acetoclastic methanogenesis reactor 106 also includes a gas transfer line 124 for transferring gases generated in reactor 106 into ERCHD electrochemical reactor 112. Reactor 112 includes a gas vent line 114 to vent methane for storage and later use, a liquid transfer line 116 and hydrogen transfer line 118, both of which are in fluid communication with hydrogenotrophic methanogenesis bioreactor 120.

Figure 1B:
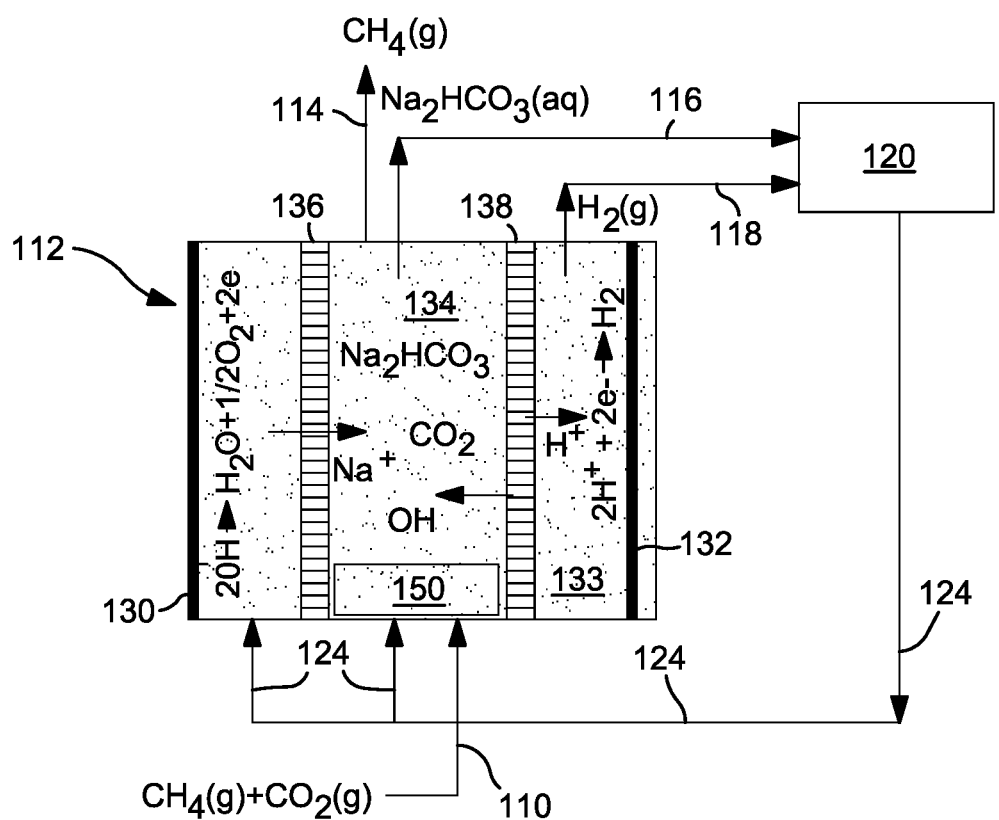
FIG. 1B provides a more detailed illustration of an embodiment of the electrochemical reactor of the system in FIG. 1A.

FIG. 1B provides a more detailed illustration of an embodiment of the electrochemical reactor of the system in FIG. 1A. Reactor 112 comprises anode 130 and cathode 132 with resin wafer 134 therebetween. Cation exchange membrane 136 separates anode 130 from resin wafer 134. Optional porous gas and liquid distributor 150 is positioned at the end of resin wafer 134 where gas and liquid are introduced into the wafer. Bipolar membrane 138 separates resin wafer 134 from cathode 132. Reactor 112 includes a gas vent line 114, a liquid transfer line 116 in fluid communication with hydrogenotrophic methanogenesis bioreactor 120 for transferring aqueous bicarbonate into bioreactor 120 during use. Hydrogen transfer line 118 provides fluid communication between bio reactor 120 and region 133 between cathode 132 and bipolar membrane 138 for transferring hydrogen generated at cathode 132 into bioreactor 120 during use. In some preferred embodiments gas and liquid distributor 150 is a microporous polymeric foam, which distributes the entering gas and liquid evenly across the resin wafer 134 to improve the uniformity of flow within the wafer.

Figure 2:
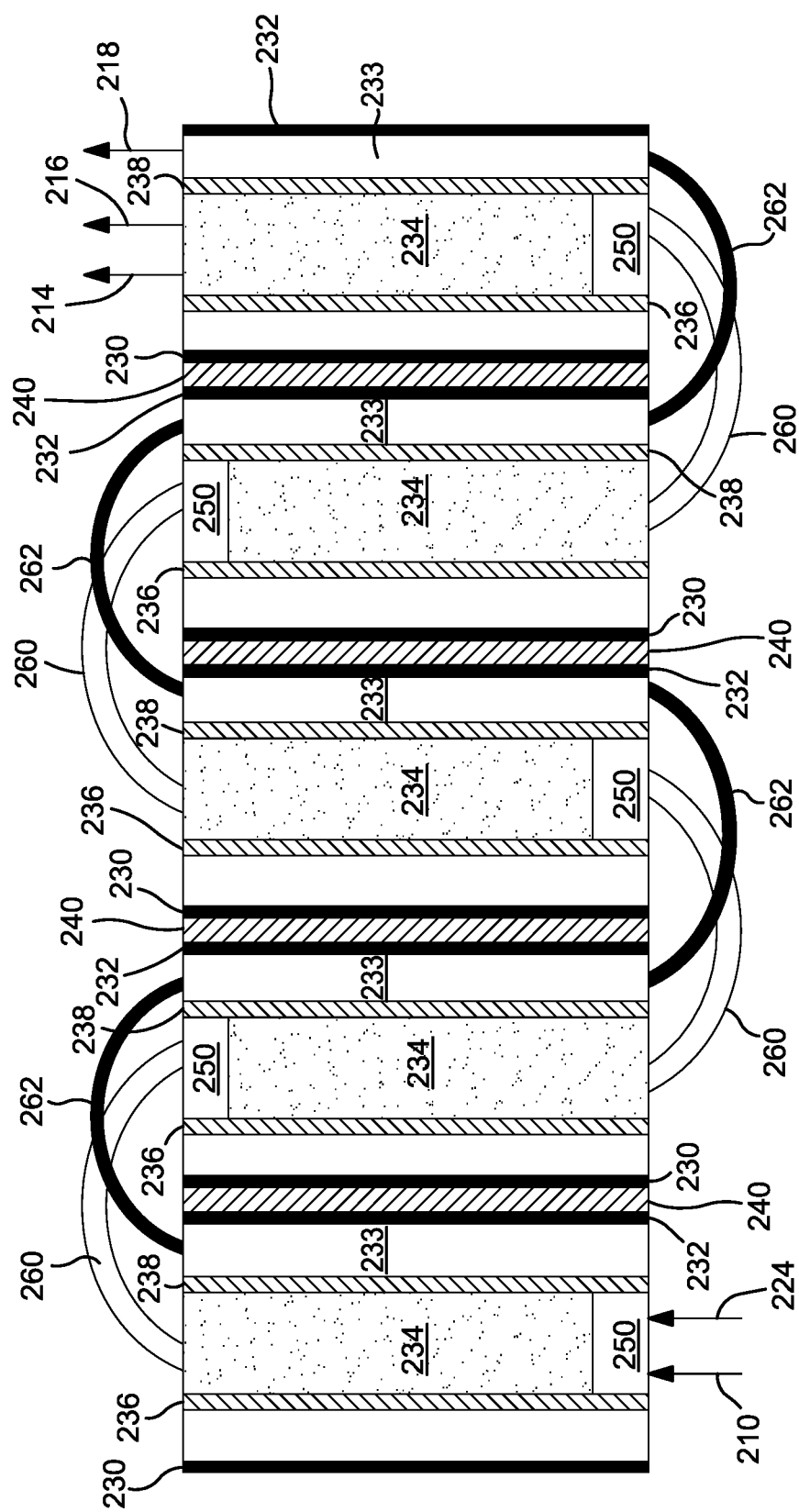
FIG. 2 is a schematic illustration of an alternative embodiment of an electrochemical reactor.

FIG. 2 is a schematic illustration of an alternative embodiment of an electrochemical reactor, which includes multiple reactor cells connected in series in a stack such that liquid and gas flow sequentially through each reactor cell, and with back to back anodes and cathodes separated by an electrical insulator. Electrochemical reactor 212 comprises anodes 230 and cathodes 232 with resin wafers 234 between the anodes and the cathodes. Cation exchange membranes 236 separates anodes 230 from resin wafers 234. Bipolar membranes 238 separates resin wafers 234 from cathodes 232. Each anode 230 is adjacent a cathode 232 of an adjacent reactor cell, with an electrical insulator 240 between the adjacent anodes and cathodes. Reactor 212 includes a gas vent line 214, a liquid transfer line 216 in fluid communication with hydrogenotrophic methanogenesis bioreactor 220 for transferring aqueous bicarbonate into bioreactor 220 during use. Hydrogen transfer line 218 provides fluid communication between bio reactor 220 and hydrogen collecting regions 233 between cathodes 232 and bipolar membranes 238 for transferring hydrogen generated at cathodes 232 into bioreactor 220 during use. Each reactor cell is in fluid communication with its closest adjacent cell so that the liquid and gas flow serially through each cell with gas and liquid initially entering the first cell in the stack and ultimately existing from the last cell in the stack. In particular the resin wafer 234 of the first cell serially in fluid communication with each subsequent resin wafer 234 by conduits 260; hydrogen collecting region 233 of the first cell in the stack is serially in fluid communication with each subsequent region 233 by conduits 262; and hydrogen transfer line 218 is in direct fluid communication with region 233 of the last cell in the stack. Similarly, gas vent 214 and liquid transfer line 216 are in direct fluid communication with the last cell in the stack; while gas transfer lines 210 and 224 are in direct fluid communication with the first cell in the stack. Each resin wafer 234 is in fluid communication with an optional gas and liquid distributor 250 at the end of the resin wafer where liquid and gas enter.

Figure 3:
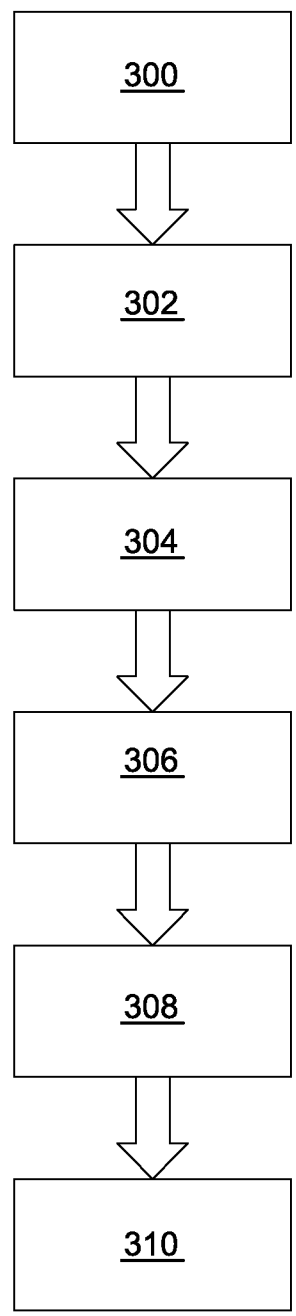
FIG. 3 provides a flow diagram of a method for generating biological methane with reduced carbon dioxide content.

Referring now to FIG. 3, a flow diagram of a method for generating renewable methane from organic materials is provided. Step 300 involves generating a biogas comprising methane and carbon dioxide by anaerobic degradation of biological material in an anaerobic digester. Step 302 is passing the biogas generated in step 300 through a electrochemical reactor comprising an anode spaced from a cathode by a porous ion exchange resin wafer with a cation exchange membrane between the anode and the resin wafer and a bipolar ion exchange membrane between the cathode and the resin wafer, while applying a voltage across the anode and the cathode to convert carbon dioxide in the biogas to bicarbonate and to generate hydrogen gas by electrochemical water splitting at the cathode. Step 304 is venting and collecting the methane from the biogas that passes through the electrochemical reactor. Step 306 is passing the hydrogen and bicarbonate formed in step 302 into a hydrogenotrophic methanogenesis bioreactor. Step 308 is generating methane from the hydrogen and bicarbonate in the hydrogenotrophic methanogenesis bioreactor. And step 310 is venting and collecting the methane that forms in the hydrogenotrophic methanogenesis bioreactor.

Figure 4:
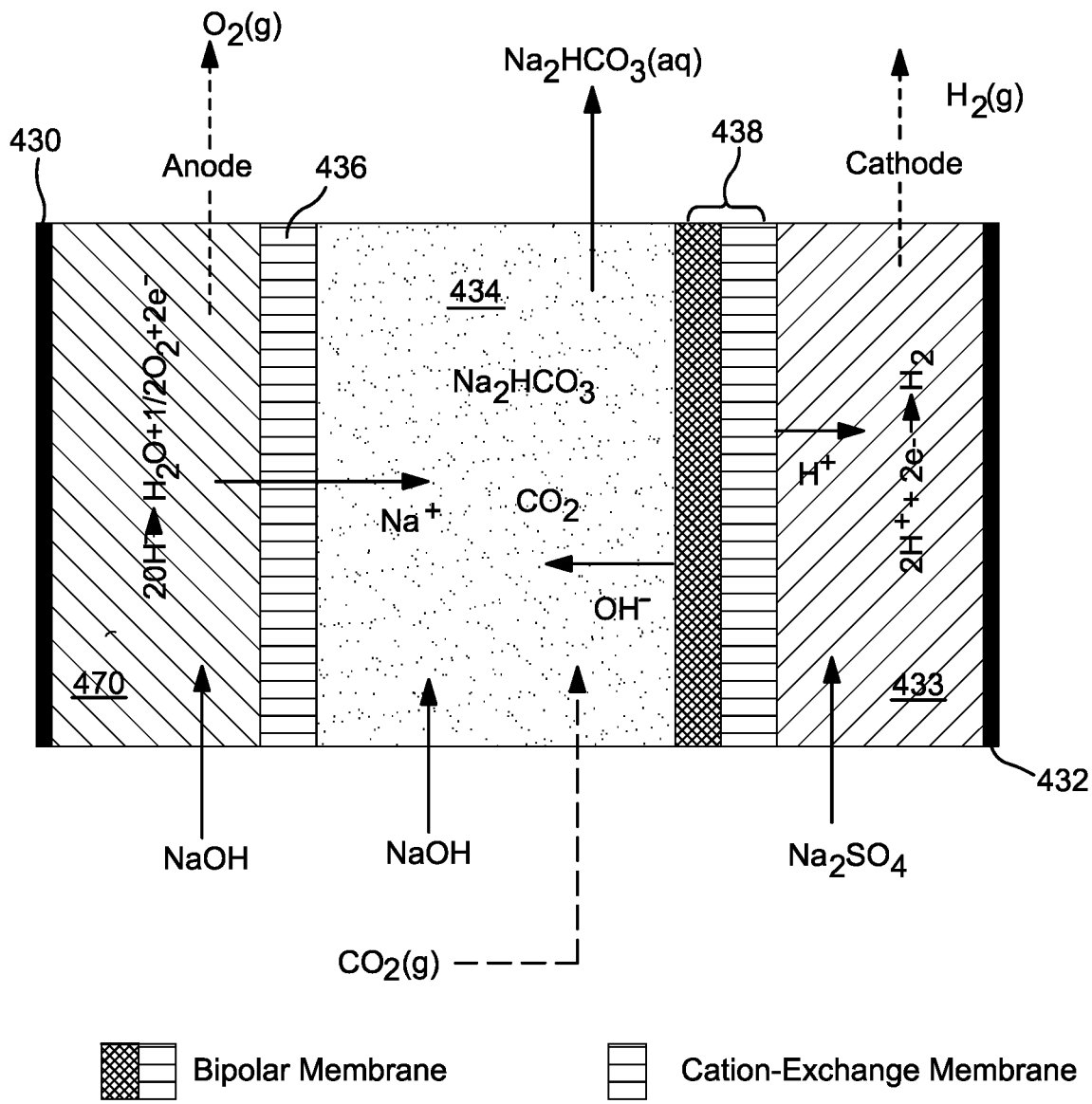
FIG. 4 schematically illustrates an apparatus for evaluating carbon dioxide removal from a gas stream using an electrochemical reactor.

Example 1. Evaluation of Electrochemical Removal of Carbon Dioxide from a Gas Stream in an Electrochemical Reactor An ERCHD comprising a single electrochemical reactor cell was assembled to demonstrate the concept of simultaneous $CO_2$ capture and hydrogen production via electrochemical reaction as shown in FIG. 4. The apparatus in FIG. 4 comprises an anode 430 and a cathode 432, with a resin wafer 434 therebetween. A cation exchange membrane 436 separates anode 432 from resin wafer 434 and a bipolar membrane 438 separates cathode 432 from resin wafer 434. Carbon dioxide and aqueous sodium hydroxide are fed into resin wafer 434 through feed line 410 while a voltage is applied across the anode and the cathode. Hydrogen generated in the region between bipolar membrane 438 and cathode 432 is vented and collected at hydrogen transfer line 418, and aqueous bicarbonate and remaining gaseous carbon dioxide exit resin wafer 434 through outlet 416.

There are three flow compartments, from right to left in the apparatus off FIG. 4: (1) An anodic compartment 270 between anode 430 and cation exchange membrane 436, filled with an anolyte solution of 10 mM NaOH (2) a $CO_2$ capture compartment comprising the resin wafer 434 and bipolar membrane 438 filled with 1 mM NaOH and $CO_2$ gas; and (3) a cathodic compartment 433 adjacent cathode 432 filled with a catholyte of 2.5 wt % $Na_2SO_4$.

During the experiments, the $CO_2$ content in the gas phase and liquid phase were measured and analyzed in the inlet and outlet of the $CO_2$ capture compartment. Hydrogen gas produced in the cathodic compartment was also measured. Samples were taken with and without the applied electric field. The results are shown in tabular format in Tables 1, 2, and 3 for three different runs, FIG. 5, and FIG. 6. $CO_2$ contents in the outlet gas phase (measured as percentage in the air) and in the outlet liquid phase (presented in bicarbonate form and measured as Total Inorganic Carbon (TIC)) were recorded in Tables 1-3.

TABLE 1

| | | Sample | % $CO_2$* | TIC (mg/L) | TIC (mM) |
|---|---|---|---|---|---|
| Samples from $CO_2$ tank and feed tank | | — | 19.0% | 46.15 | 3.85 |
| Samples | no gas or liquid flow | — | 0.2% | — | — |
| from | flow, no voltage | 1 | 13.1% | 58.89 | 4.91 |
| gas/liquid | gas liquid flow, 1.2 V | 2 | 14.1% | 63.19 | 5.27 |
| separator | | 3 | 15.4% | 63.54 | 5.30 |
| | | 4 | 16.2% | 69.15 | 5.76 |

*excluding broad peaks at 0.7 and 6.7 min

TABLE 2

| | | Sample | % $CO_2$ | TIC (mg/L) | TIC (mM) |
|---|---|---|---|---|---|
| Samples from $CO_2$ tank and feed tank | | — | 19.0% | 38.63 | 3.22 |
| Samples | no gas or liquid flow | — | 0.4% | — | — |
| from | flow, no voltage | 1 | 10.7% | 45.67 | 3.81 |
| gas/liquid | gas liquid flow, 10 V | 2 | 12.3% | 47.23 | 3.94 |
| separator | | 3 | 12.6% | 50.16 | 4.18 |
| | | 4 | 13.0% | 50.26 | 4.19 |
| | | 5 | 13.0% | 51.42 | 4.29 |
| | | 6 | 12.8% | 54.12 | 4.51 |
| | | 7 | 12.9% | 57.62 | 4.80 |

TABLE 3

| | | Sample | Time (min) | % $CO_2$ | TIC (mg/L) | TIC (mM) |
|---|---|---|---|---|---|---|
| Samples from $CO_2$ tank & feed tank | | — | — | 20.6% | 3.15 | 0.26 |
| Samples | no gas or liquid flow | 0 | 0 | 1.1% | — | — |
| from | flow, no voltage | 1 | 15 | 12.1% | 24.15 | 2.01 |
| gas/liquid | gas liquid flow, | 2 | 30 | 14.0% | 31.07 | 2.59 |
| separator | 1.2 V | 3 | 45 | 11.2% | 29.98 | 2.50 |
| | | 4 | 75 | 10.3% | 31.65 | 2.64 |
| | | 5 | 105 | 10.4% | 27.90 | 2.33 |
| | | 6 | 135 | 10.9% | 27.69 | 2.31 |

Figure 5:
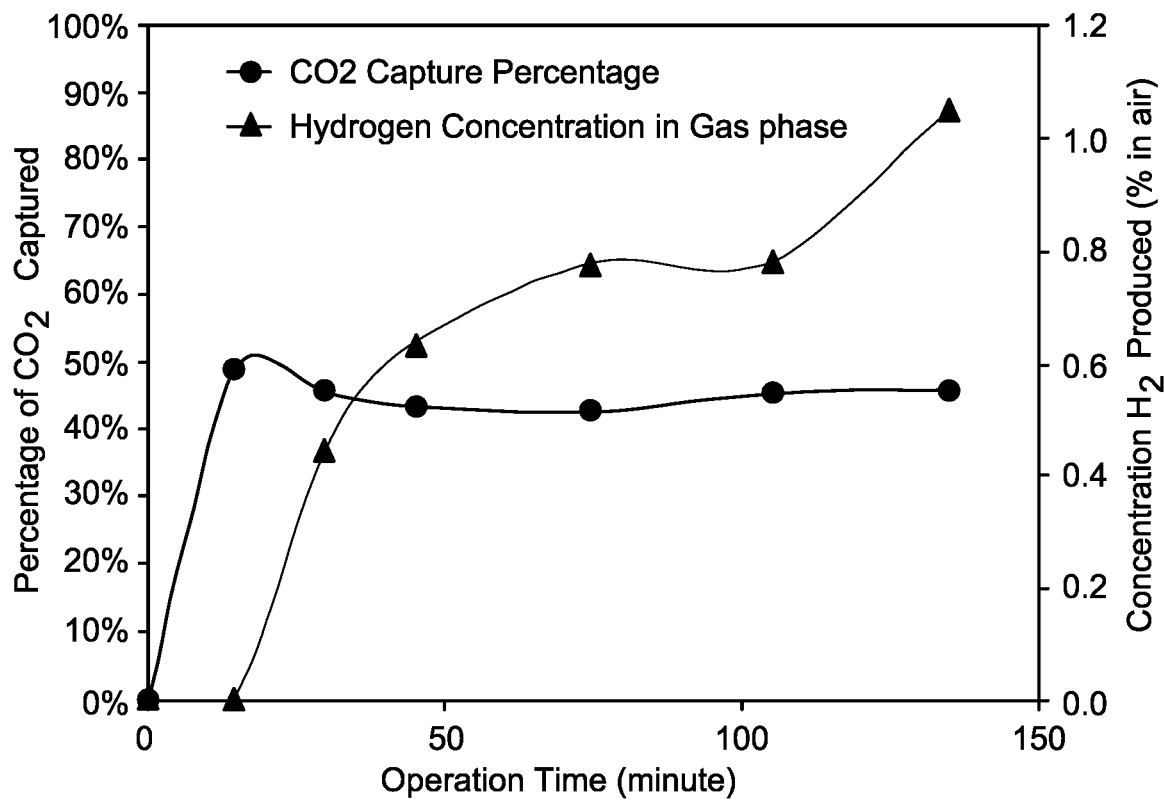
FIG. 5 provides plots of percentage carbon dioxide captured and concentration of hydrogen produced versus operation time, for the apparatus of FIG. 4.
Figure 6:
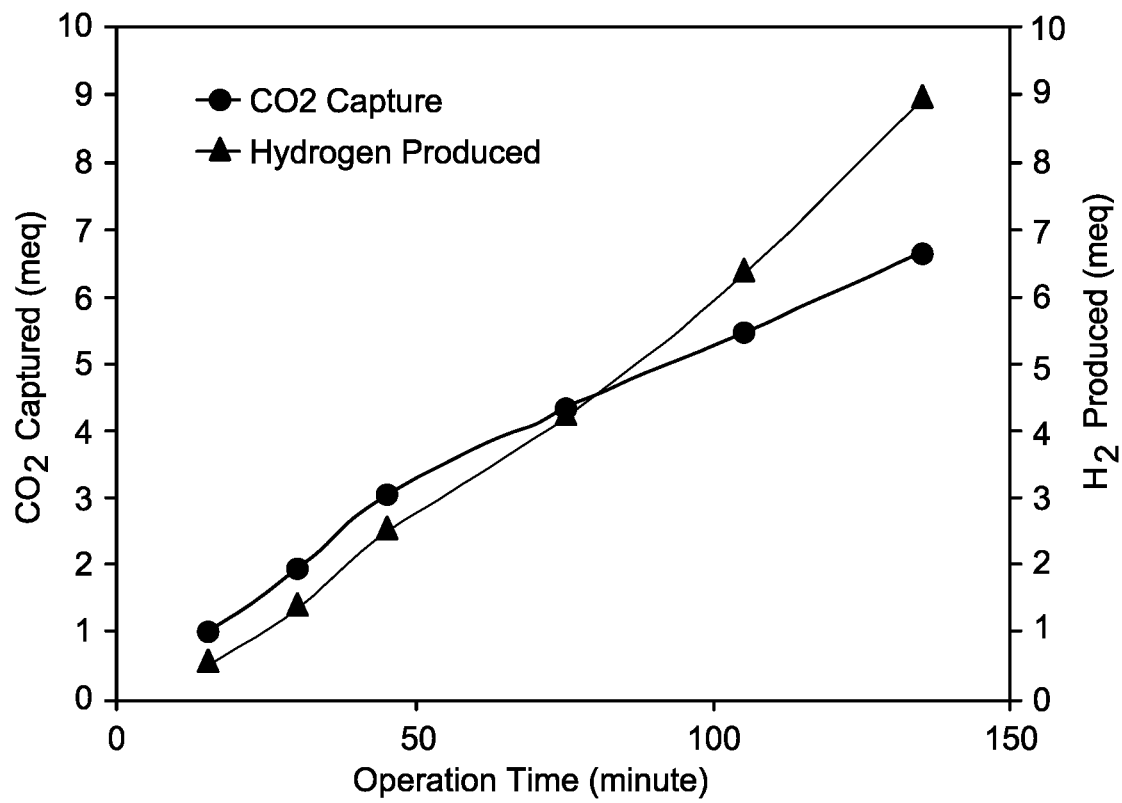
FIG. 6 provides plots of carbon dioxide captured in milliequivalents (meq) and hydrogen produced (meq) versus operation time, for the apparatus of FIG. 4.

Low electric field (Table 1, 1.2 V) and high applied field (Table 2 and 3, 10 V) have an impact on the $CO_2$ capture rate. FIG. 5 shows the $CO_2$ capture percentage and hydrogen content in the air during the operation. FIG. 6 shows the mass balance of $CO_2$ capture and hydrogen production during the operation, almost equal molar amounts of $CO_2$ were captured when the hydrogen also was produced (i.e., when a voltage was applied). These results show that an ERCHD system with simultaneous $CO_2$ capture and hydrogen production in is more efficient at $CO_2$ capture than just $CO_2$ capture without hydrogen production.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The embodiments of the invention in which an exclusive property or privilege is claimed are defined as follows:

1. A system for biologically generating methane and removing carbon dioxide therefrom, the system comprising:
    (a) a primary anaerobic digester adapted and arranged to generate a gaseous mixture comprising methane and carbon dioxide from organic materials;
    (b) an electrochemical reactor; and
    (c) a hydrogenotrophic methanogenesis bioreactor adapted and arranged to convert the bicarbonate and hydrogen from the electrochemical reactor to methane;
    wherein:
    the electrochemical reactor comprises a plurality reactor cells in a stack with each reactor cell including:
    an anode;
    a cathode spaced from the anode;
    a single porous ion exchange resin wafer between the anode and the cathode, wherein the ion exchange resin wafer consists of a basic ion exchange resin wafer;
    a cation exchange membrane adjacent to the anode between the anode and the resin wafer, wherein the cation exchange membrane is adjacent to both the anode and the resin wafer; and
    a bipolar ion exchange membrane between the cathode and the resin wafer, wherein the bipolar exchange membrane is adjacent to both the cathode and the resin wafer;
    wherein:
    the cathode of each adjacent reactor cell is separated from the anode of the nearest adjacent cell by an electrical insulator;
    the reactor cells are in fluid communication with each other in series so that liquid and gas flow through each resin wafer sequentially; and
    the electrochemical reactor includes a hydrogen transfer line to direct hydrogen gas from the cathodes out of the electrochemical reactor;
    the electrochemical reactor is adapted and arranged to capture gaseous carbon dioxide within the resin wafer as aqueous bicarbonate, and to electrochemically generate hydrogen gas at the cathodes when an aqueous liquid and a carbon dioxide-containing gas are flowing through the reactor cells, and a voltage is applied across the anode and the cathode of each reactor cell;
    the primary anaerobic digester includes a gas transfer line in fluid communication with an inlet end of the electrochemical reactor adapted and arranged to receive gas and liquid into pores of the resin wafer;
    the electrochemical reactor further includes a first gas vent line; an outlet operably connected to a liquid transfer line in fluid communication with the hydrogenotrophic methanogenesis bioreactor; and a hydrogen transfer line providing fluid communication between the hydrogenotrophic methanogenesis bioreactor and a region adjacent the cathode where hydrogen is generated during use; and
    the hydrogenotrophic methanogenesis bioreactor comprises: a liquid recycle line in fluid communication with the inlet end of the electrochemical reactor adapted and arranged to direct fluid flow through the electrochemical reactor; and a second gas vent line;
    wherein in use, the electrochemical reactor is filled with an aqueous fluid; the gaseous mixture containing methane and carbon dioxide is formed from the organic materials in the primary anaerobic digester; and the gaseous mixture is transferred from the primary anaerobic digester via the gas transfer line into the inlet end of the electrochemical reactor to flow through the resin wafer while a voltage is applied across the cathode and the anode; the carbon dioxide from the gaseous mixture is electrochemically converted to bicarbonate in the aqueous fluid within electrochemical reactor; hydrogen is electrochemically generated at the cathode; the methane from the gaseous mixture and the aqueous fluid both flow through the resin wafer, and carbon dioxide-depleted methane is vented through the first gas vent line and stored for later use; the aqueous fluid containing the bicarbonate flows through the liquid transfer line into the hydrogenotrophic methanogenesis bioreactor, and the hydrogen generated at the cathode flows through the hydrogen transfer line into the hydrogenotrophic methanogenesis bioreactor, where the bicarbonate and hydrogen are biologically converted to methane; the methane generated in the hydrogenotrophic methanogenesis bioreactor is vented through the second gas vent line and collected for later use; and aqueous fluid is recycled back into the inlet end of the electrochemical reactor from the hydrogenotrophic methanogenesis bioreactor through the liquid recycle line.

2. The system of claim 1, wherein the primary anaerobic digester comprises:
    (i) an acidogenesis reactor adapted and arranged to biologically convert organic waste and wastewater to soluble volatile fatty acids (VFA), methane, carbon dioxide, and hydrogen; and
    (ii) an acetoclastic methanogenesis reactor adapted and arranged to biologically convert the VFA to carbon dioxide and methane;
    wherein the gas transfer line is in fluid communication with both the acidogenesis reactor and the acetoclastic methanogenesis reactor; and the acidogenesis reactor is in fluid communication with the acetoclastic methanogenesis reactor via a liquid feed line; and
    wherein in use, VFA, carbon dioxide, hydrogen and methane are generated in the acidogenesis reactor; VFA-containing liquid from the acidogenesis reactor is fed into the acetoclastic methanogenesis reactor via the liquid feed line; methane and carbon dioxide are generated in the acetoclastic methanogenesis reactor, and carbon dioxide, methane, and hydrogen are transferred from the acidogenesis reactor and the acetoclastic methanogenesis reactor into the inlet end of electrochemical reactor through the gas transfer line.

3. The system of claim 1, wherein each of the reactor cells comprises at least one porous gas and liquid flow distributor in contact with the resin wafer thereof; the flow distributor being adapted and arranged to laterally distribute gas and liquid within pores thereof prior to entering the resin wafer of the electrochemical reactor.

4. The system of claim 3, wherein the at least one porous gas and liquid flow distributor includes interconnected pores having an average pore size in the range of about 100 to about 600 micrometers, and is adapted and arranged to laterally distribute the liquid and gas bubbles having an average diameter in the range of about 100 to about 600 micrometers throughout the flow distributor and into the resin wafer of the electrochemical reactor.

5. The system of claim 1, wherein the electrochemical reactor comprises at least one porous gas and liquid flow distributor in contact with at least one of the resin wafers in the stack; and the at least one porous gas and liquid flow distributor is adapted and arranged to distribute gas within the liquid flowing through the resin wafers of the electrochemical reactor.

6. The system of claim 5, wherein the at least one porous gas and liquid flow distributor includes interconnected pores having an average pore size in the range of about 100 to about 600 micrometers, and is adapted and arranged to laterally distribute the liquid and gas bubbles having an average diameter in the range of about 100 to about 600 micrometers throughout the flow distributor and into the resin wafers of the electrochemical reactor.

7. The system of claim 1, wherein each wafer has a thickness in the range of about 1 to about 20 mm.

8. The system of claim 1, wherein the electrochemical reactor comprises 2 to about 50 reactor cells.

9. An electrochemical reactor for capturing carbon dioxide as bicarbonate and generating hydrogen; the reactor comprising a plurality reactor cells in a stack with each reactor cell including:
(a) an anode;
(b) a cathode spaced from the anode;
(c) a single porous ion exchange resin wafer between the anode and the cathode, wherein the ion exchange resin wafer consists of a basic ion exchange resin wafer;
(d) a cation exchange membrane between the anode and the resin wafer, wherein the cation exchange membrane is adjacent to both the anode and the resin wafer; and
(e) a bipolar ion exchange membrane between the cathode and the resin wafer, wherein the bipolar exchange membrane is adjacent to both the cathode and the resin wafer;
wherein:
(A) the cathode of each adjacent reactor cell is separated from the anode of the nearest adjacent cell by an electrical insulator;
(B) the reactor cells are in fluid communication with each other in series so that liquid and gas flow through each resin wafer sequentially; and
(C) the electrochemical reactor includes a hydrogen transfer line to direct hydrogen gas from the cathodes out of the electrochemical reactor; and
the electrochemical reactor is adapted and arranged to capture gaseous carbon dioxide within the resin wafer as aqueous bicarbonate, and to electrochemically generate hydrogen gas at the cathodes when an aqueous liquid and a carbon dioxide-containing gas are flowing through the reactor cells, and a voltage is applied across the anode and the cathode of each reactor cell.

10. The electrochemical reactor of claim 9, further comprising a gas vent line for venting a carbon dioxide depleted gas from the resin wafers of the electrochemical reactor.

11. The electrochemical reactor of claim 9, wherein the electrochemical reactor comprises at least one porous gas and liquid flow distributor in contact with at least one of the resin wafers in the stack; and the at least one porous gas and liquid flow distributor is adapted and arranged to distribute gas within the liquid flowing through the resin wafers of the electrochemical reactor.

12. The electrochemical reactor of claim 11, wherein the at least one porous gas and liquid flow distributor includes interconnected pores having an average pore size in the range of about 100 to about 600 micrometers, and is adapted and arranged to laterally distribute the liquid and gas bubbles having an average diameter in the range of about 100 to about 600 micrometers throughout the distributor and into the resin wafers of the electrochemical reactor.

13. The electrochemical reactor of claim 9, wherein each wafer has a thickness in the range of about 1 to about 20 mm.

14. The electrochemical reactor of claim 9, wherein the electrochemical reactor comprises 2 to about 50 reactor cells.

15. A method for biologically generating carbon dioxide-depleted biogas comprising the steps of:
(a) generating a biogas comprising methane and carbon dioxide by anaerobic degradation of biological material in an anaerobic digester;
(b) passing the biogas generated in step (a) through the electrochemical reactor of claim 10, while applying a voltage across the anode and the cathode to convert carbon dioxide in the biogas to bicarbonate and to generate hydrogen gas by electrochemical water splitting at the cathode;
(c) venting and collecting the methane from the biogas that passes through the electrochemical reactor;
(d) passing the hydrogen and bicarbonate formed in step (b) into a hydrogenotrophic methanogenesis bioreactor;
(e) generating methane from the hydrogen and bicarbonate in the hydrogenotrophic methanogenesis bioreactor; and
(f) venting and collecting the methane that forms in the hydrogenotrophic methanogenesis bioreactor.

16. The method of claim 15, wherein the anaerobic digester comprises:
(i) an acidogenesis reactor adapted and arranged to biologically convert organic waste and wastewater to soluble volatile fatty acids (VFA), methane, carbon dioxide, and hydrogen; and
(ii) an acetoclastic methanogenesis reactor adapted and arranged to biologically convert the VFA to carbon dioxide and methane;
wherein in use, VFA, carbon dioxide, hydrogen and methane are generated in the acidogenesis reactor; VFA-containing liquid from the acidogenesis reactor is fed into the acetoclastic methanogenesis reactor; methane and carbon dioxide are generated in the acetoclastic methanogenesis reactor, and carbon dioxide, methane, and hydrogen are transferred from the acidogenesis reactor and the acetoclastic methanogenesis reactor into electrochemical reactor.

17. The method of claim 15, wherein the electrochemical reactor comprises at least one porous gas and liquid flow distributor in contact with at least one of the resin wafers in the stack; and the at least one gas distributor is adapted and arranged to distribute gas within the liquid flowing through the resin wafers of the electrochemical reactor.

18. The method of claim 17, wherein the at least one porous gas and liquid flow distributor includes interconnected pores having an average pore size in the range of about 100 to about 600 micrometers, and is adapted and arranged to laterally distribute the liquid and gas bubbles having an average diameter in the range of about 100 to about 600 micrometers throughout the flow distributor and into the resin wafers of the electrochemical reactor.

19. The apparatus of claim 9 wherein each electrical insulator comprises a non-conductive polymer.

* * * * *